(12) United States Patent
Thomas et al.

(10) Patent No.: US 9,773,230 B2
(45) Date of Patent: Sep. 26, 2017

(54) PROVIDING USER-DEFINED MESSAGES

(75) Inventors: Todd Thomas, Lester Prairie, MN (US); Gregory Zelenak, Fridley, MN (US)

(73) Assignee: McKesson Corporation, San Francisco, CA (US)

( * ) Notice: Subject to any disclaimer, the term of this patent is extended or adjusted under 35 U.S.C. 154(b) by 756 days.

(21) Appl. No.: 13/295,568

(22) Filed: Nov. 14, 2011

(65) Prior Publication Data

US 2013/0124645 A1 May 16, 2013

(51) Int. Cl.
| | | |
|---|---|---|
| G06F 15/16 | (2006.01) | |
| G06Q 10/10 | (2012.01) | |
| G06Q 50/24 | (2012.01) | |
| H04L 12/58 | (2006.01) | |

(52) U.S. Cl.
CPC ........... *G06Q 10/107* (2013.01); *G06Q 50/24* (2013.01); *H04L 51/063* (2013.01); *H04L 51/066* (2013.01); *H04L 51/24* (2013.01)

(58) Field of Classification Search
CPC ...... H04L 51/063; H04L 51/066; H04L 51/24
USPC .................................................. 709/206–207
See application file for complete search history.

(56) References Cited

U.S. PATENT DOCUMENTS

| | | | |
|---|---|---|---|
| 2005/0203384 A1* | 9/2005 | Sati | A61B 6/547 600/426 |
| 2006/0265508 A1* | 11/2006 | Angel et al. | 709/230 |
| 2009/0083231 A1* | 3/2009 | Eberholst et al. | 707/3 |
| 2009/0319535 A1* | 12/2009 | Webber et al. | 707/10 |
| 2011/0029326 A1* | 2/2011 | Venon | 705/3 |
| 2011/0276338 A1* | 11/2011 | Warner et al. | 705/2 |
| 2011/0295961 A1* | 12/2011 | Wilkes et al. | 709/206 |
| 2013/0076157 A1* | 3/2013 | Stein | A61F 2/442 307/116 |
| 2013/0093829 A1* | 4/2013 | Rosenblatt | G09B 5/00 348/14.01 |

* cited by examiner

*Primary Examiner* — Jason Recek
(74) *Attorney, Agent, or Firm* — Alston & Bird LLP

(57) ABSTRACT

Systems, methods, apparatus, and computer program products provide user-defined messages. In one embodiment, user-defined messaging configurations can be defined. Then, a record queue can be monitored for the entry of new records. New records can be evaluated to determine whether they are associated with user-defined messaging configurations. For the records so associated, reports defined in the user-defined messaging configurations can be requested and used to create user-defined messages.

21 Claims, 14 Drawing Sheets

| SEQ | HL7 Element Name | HSM Field Length | HL7 Field Length | HL7 Data Type | R/O | PHS Name | Comments |
|---|---|---|---|---|---|---|---|
| | | | | | | | |

| COLUMN HEADING | DESCRIPTION |
|---|---|
| SEQ | HL7 field sequence number |
| HL7 Element Name | HL7 field description |
| HL7 Field Length | Suggested field length including all components and separators as defined by HL7 |
| HSM Field Length | HSM (or PHS) maximum field length, listed for each component |
| HL7 Data Type | HL7 data type |
| R/O | Required (R) or optional (O) field. Optional fields are not marked |
| HSM Name | SQL database table and field name (table.field). (J)'s indicate 'joined' fields |
| Comments | Examples, helpful tips, suggestions |

<message start> <HL7 message> <message terminator>

Fig. 5B

<message start> <HL7 acknowledgment> <message terminator>

<message start> is decimal 11 (ASCII VT)

<HL7 message> is any character string(s) not containing a <message start> a <message terminator> or a null, each character string must be followed by a decimal 13 (ASCII CR).

<message terminator> is two characters, decimal 28 (ASCII FS) followed by decimal 13 (ASCII CR)

| <11> | MSH¦¦¦ | <13> | PID¦¦¦ | <13> | PV1¦¦¦ | <13> | OBR¦¦¦ | <13> | OBX¦¦¦ | <28> | <13> |
|------|--------|------|--------|------|--------|------|--------|------|--------|------|------|
| [0x0B] | | [0x0D] | | [0x0D] | | [0x0D] | | [0x0D] | | [0x1C] | [0x0D] |

(numbers denoted by "<>" represent decimal characters, strings denoted by "[ ]" represent hexidecimal characters.)

<11> or [0x0B] = Vertical Tab
<13> or [0x0D] = Carriage Return
<28> or [0x1C] = File Separator
Pipe Symbol "¦" - HSM's default field separator

| SEGMENT ID | SEGMENT DESCRIPTIONS |
|---|---|
| MSH | Message Header |
| PID | Patient Identification |
| [ PV1 ] | Patient Visit Information |
| OBR | Observation Request Segment |
| {OBX} | Observation/Result Segment |

KEY:
[ ] = optional segment
{ } = 1+ occurrences, repeated

Fig. 7B

| SEGMENT ID | SEGMENT DESCRIPTIONS |
|---|---|
| MSH | Message Header |
| PID | Patient Identification |
| [ PV1 ] | Patient Visit Information |
| | [ any segments that follow are determined by report contents ] |

KEY:
[ ] = optional segment
{ } = 1+ occurrences, repeated

```
<segmentseparator>
ORC|RE|||||||CCYYMMDDHHMM|||orderedby_id^lastname^firstname|||||||

<segmentseparator>
OBR|1||15,808.00^SM||piority||CCYYMMDDHHMM|||||danger_code|put relevant clinical
info
here|||orderingpract_id^lastname^firstname||||||CCYYMMDDHHMM|||status|||||proname.
abbr^BRAIN BIOPSY, STEREOTACTIC^SM|||||||||

<segmentseparator>
OBX|1||obsevCode^observCodeName^SM|observSubCode^observSubCodeName|the important
observationData goes here||||||status||||CCYYMMDDHHMM||||
```

Fig. 13

```
MSH|^~\&|SEND APP GMZ|SEND FAC GMZ|Phase2|RECV FAC GMZ|20101018093 6||ORU^R01|1|P|2.3
PID|1||021904-3^^^ST01A^MR|T0013616^^^HS|Doe^John^A||||||1122 Ln^^Test City^IL^60090^USA|||||||021904-
C^^^ST01A|||||||N
PV1|1|O|^^^A1||||||||OP|||||||||||||||||2_FAC|||||||||||
OBR|1||215808^SM|PREOP^PreOperative^SM|||20061213213 6||||||||||||||20061213213 6||||||||^BRAIN BIOPSY,
STEREOTACTIC^SM
OBX|1||PREOP^PreOperative^SM||15808^casemain_id|||||F||||^HORIZON SURGICAL MANAGER^SM
OBX|2||PREOP^PreOperative^SM||^general case information|||||F||||^HORIZON SURGICAL MANAGER^SM
OBX|3||PREOP^PreOperative^SM||Yes^latex decision|||||F||||^HORIZON SURGICAL MANAGER^SM
OBX|4||PREOP^PreOperative^SM||^input_recorded_datetime|||||F||||^HORIZON SURGICAL MANAGER^SM
OBX|5||PREOP^PreOperative^SM||^output_recorded_datetime|||||F||||^HORIZON SURGICAL MANAGER^SM
OBX|6||PREOP^PreOperative^SM||^procedure information|||||F||||^HORIZON SURGICAL MANAGER^SM
OBX|7||PREOP^PreOperative^SM||BRAIN BIOPSY, STEREOTACTIC^actual_proname|||||F||||^MANAGEMENT
SYSTEM^SM
```

Fig. 14

PROVIDING USER-DEFINED MESSAGES

BACKGROUND

Today, clients/customers often want to send/transmit messages that contain a wide range of information/data. However, creating interfaces that can output data differently from one client/user to another often requires customizable interfaces that can be difficult to implement and support. Thus, a need exists for a solution that can offer the output of client/user-defined information/data using various standards without requiring custom interfaces.

BRIEF SUMMARY

In general, embodiments of the present invention provide systems, methods, apparatus, and computer program products for providing user-defined messages.

In accordance with one aspect, a method for providing a user-defined message is provided. In one embodiment, the method comprises (1) receiving a notification that a record is in a record queue; (2) determining whether the record is associated with a user-defined messaging configuration; (3) after determining that the record is associated with a user-defined messaging configuration, request a report for the record corresponding to the user-defined messaging configuration; and (4) generate a user-defined message based at least in part on the report for the record.

In accordance with another aspect, a computer program product for providing a user-defined message is provided. The computer program product may comprise at least one computer-readable storage medium having computer-readable program code portions stored therein, the computer-readable program code portions comprising executable portions configured to (1) receive a notification that a record is in a record queue; (2) determine whether the record is associated with a user-defined messaging configuration; (3) after determining that the record is associated with a user-defined messaging configuration, request a report for the record corresponding to the user-defined messaging configuration; and (4) generate a user-defined message based at least in part on the report for the record.

In accordance with yet another aspect, an apparatus comprising at least one processor and at least one memory including computer program code is provided. In one embodiment, the at least one memory and the computer program code may be configured to, with the processor, cause the apparatus to at least (1) receive a notification that a record is in a record queue; (2) determine whether the record is associated with a user-defined messaging configuration; (3) after determining that the record is associated with a user-defined messaging configuration, request a report for the record corresponding to the user-defined messaging configuration; and (4) generate a user-defined message based at least in part on the report for the record.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 1:
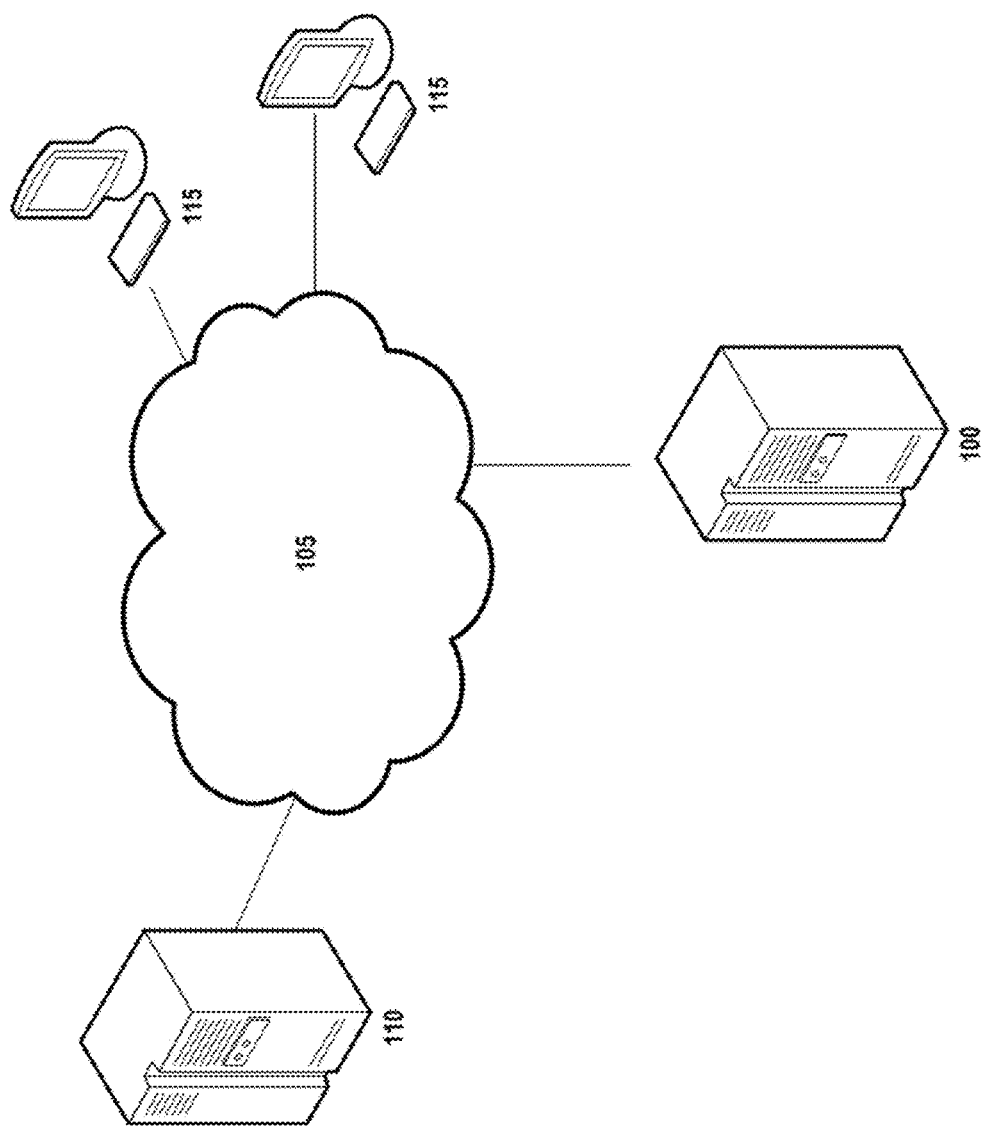
FIG. 1 is an overview of a system according to various embodiments of the present invention.

FIGS. 4, 5A, 5B, 6, 7A, and 7B show exemplary message formats that can be used in accordance with various embodiments of the present invention.

Figure 8:
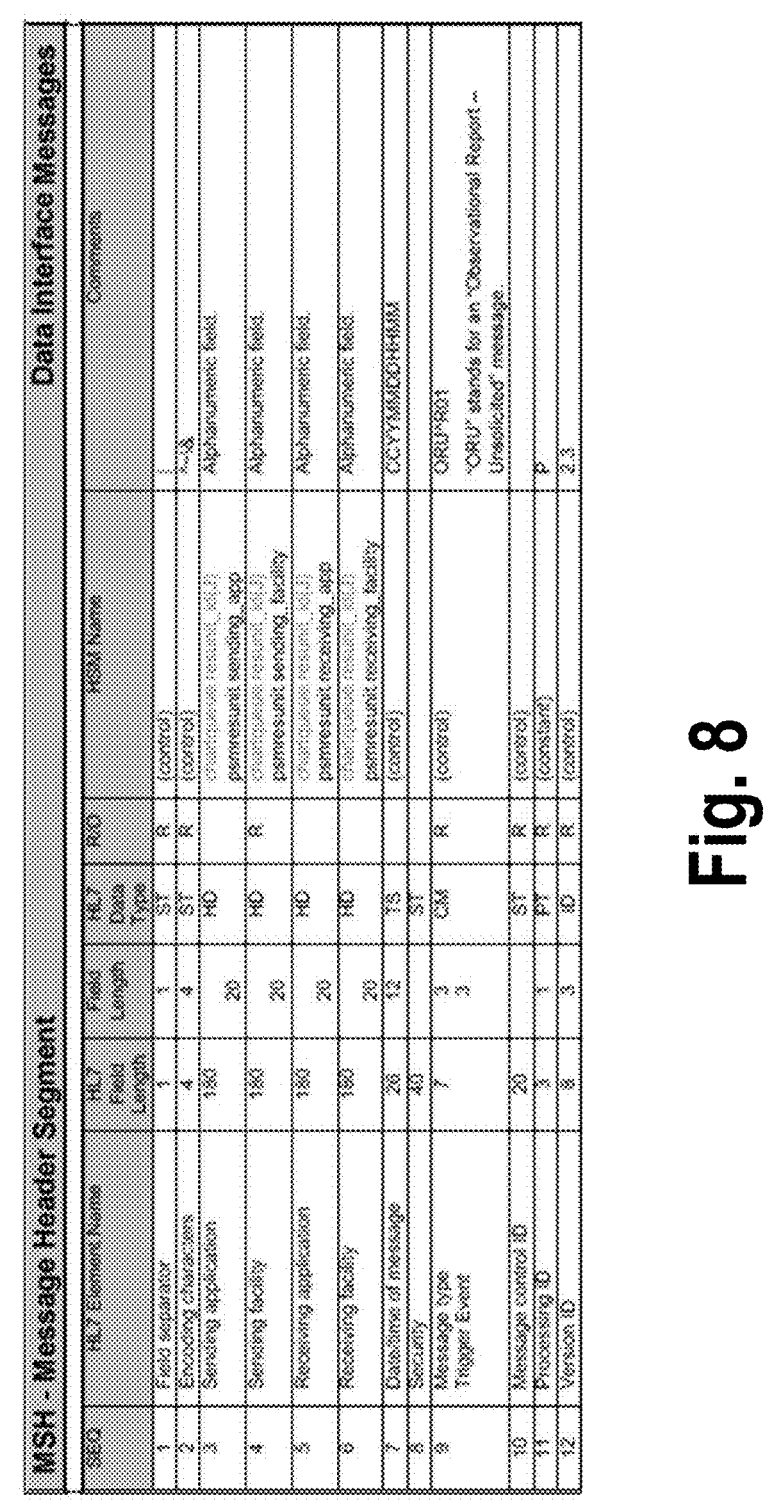
Figure 9:
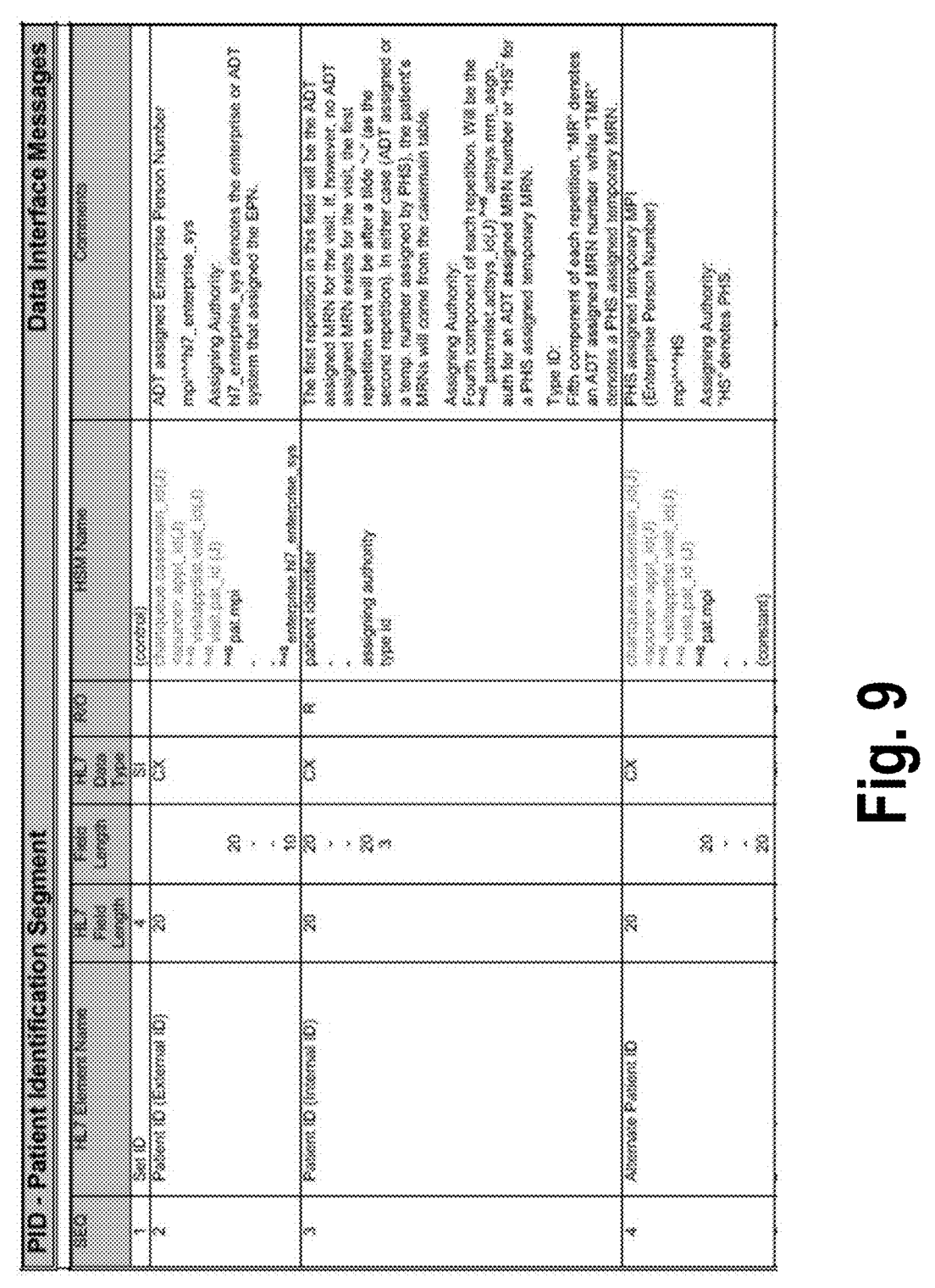
Figure 10:
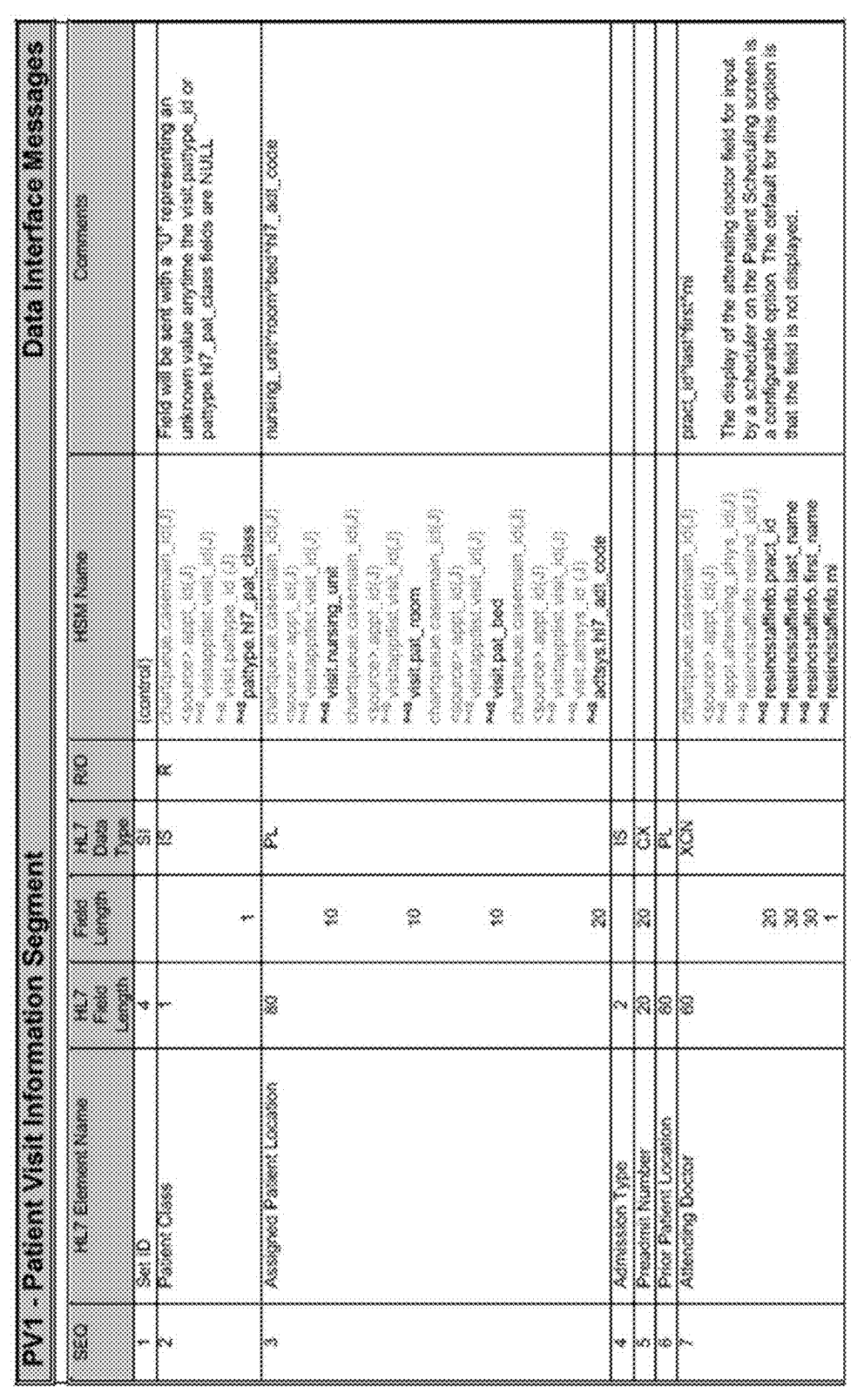
Figure 11:
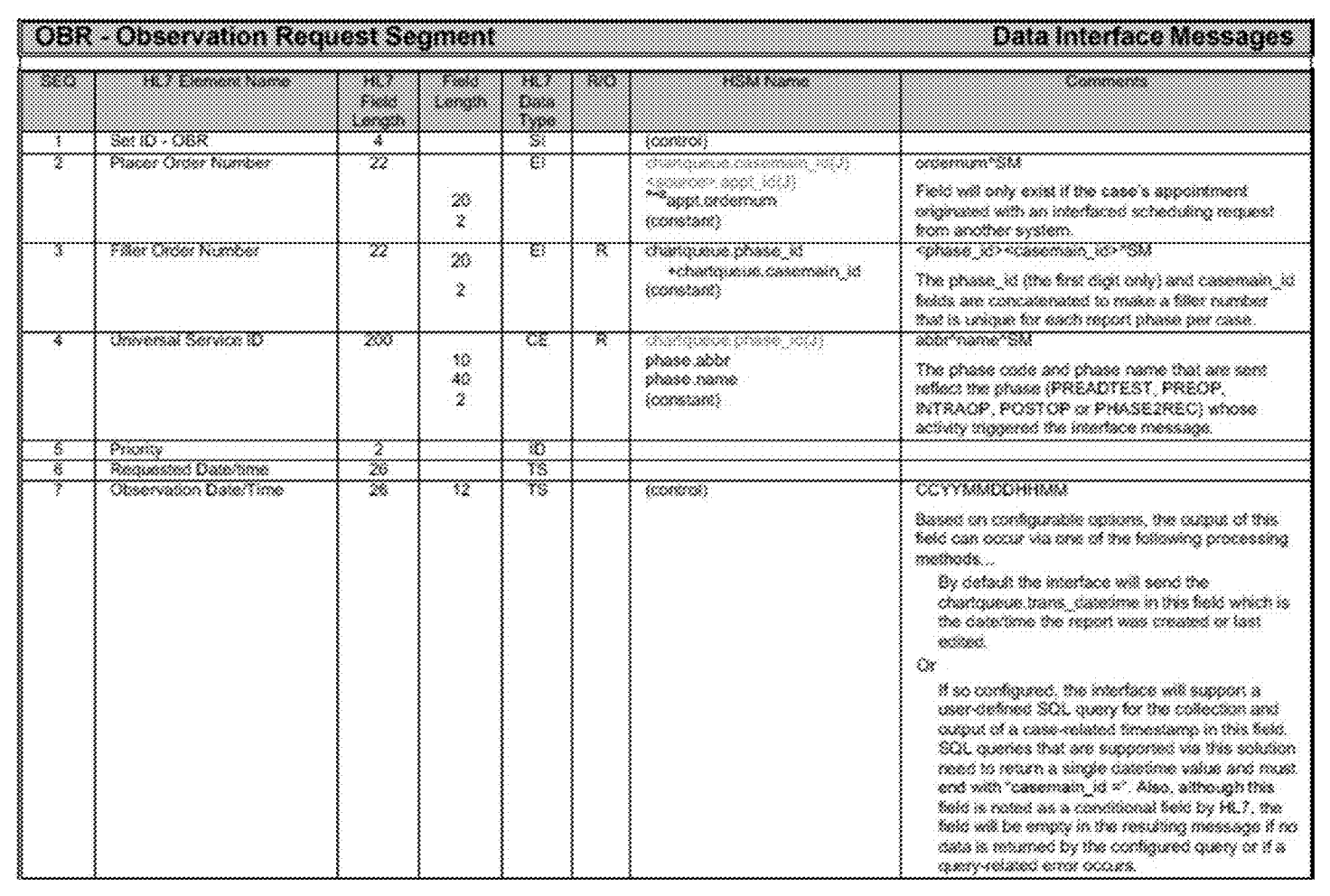
Figure 12:
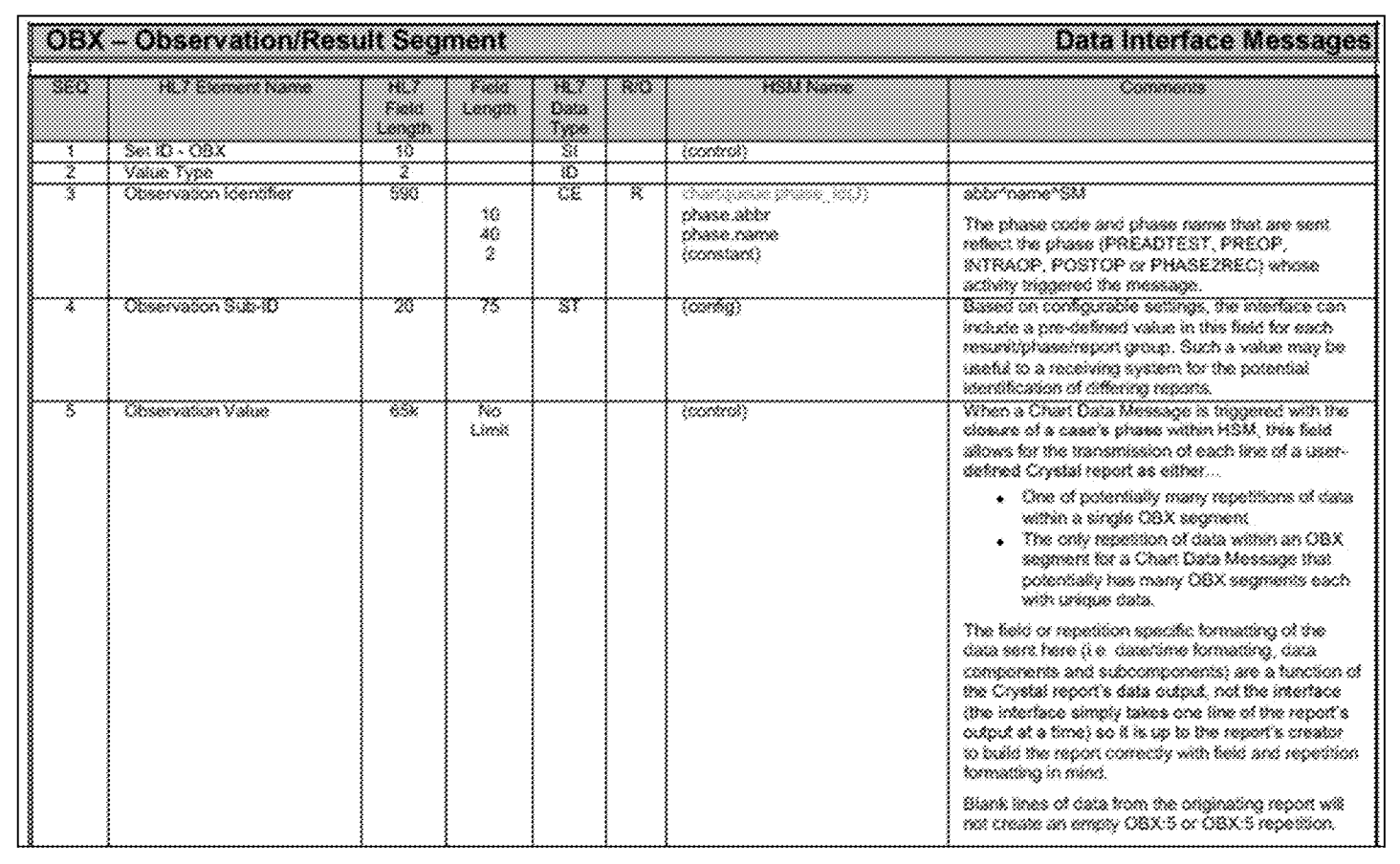

FIGS. 8-12 show the correlation of exemplary message formats that can be used in accordance with various embodiments of the present invention.

FIG. 13 shows an exemplary report that can be used with various embodiments of the present invention.

FIG. 14 shows an exemplary user-defined message that can be generated with various embodiments of the present invention.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. METHODS, APPARATUS, SYSTEMS, AND COMPUTER PROGRAM PRODUCTS

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

II. GENERAL OVERVIEW

In general, according to various embodiments of the present invention, methods, apparatus, systems, and computer program products are provided for providing user-defined messages. A system according to a particular embodiment may include one or more management computing entities, one or more networks, one or more data interface computing entities (e.g., with data interfaces), and one or more client/user computing entities. In one embodiment, a user-defined messaging configuration can define/identify a report format that allows for a client/user defined report to be created/generated/constructed in a way that simulates, for example, HL7 order-related segments and the fields/data they contain. Then, in one embodiment, based on certain triggers and interface processing, the data interface computing entity (e.g., with a data interface) can create/generate/construct, for instance, a non-order-related "shell" of an HL7 order message. The data interface computing entity (e.g., with a data interface) can then request the defined/identified report according to the user-defined messaging configuration. The data interface computing entity (e.g., with a data interface) can select the text from the report and combine the text with the message shell that meets the client's/user's needs to create a user-defined message.

III. EXEMPLARY SYSTEM ARCHITECTURE

FIG. 1 provides an illustration of a system that can be used in conjunction with various embodiments of the present invention. As shown in FIG. 1, the system may include one or more management computing entities 100, one or more networks 105, one or more data interface computing entities 110 (e.g., with data interfaces), and one or more client/user computing entities 115. Each of the components of the system may be in electronic communication with, for example, one another over the same or different wireless or wired networks including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

1. Exemplary Management Computing Entity

Figure 2:
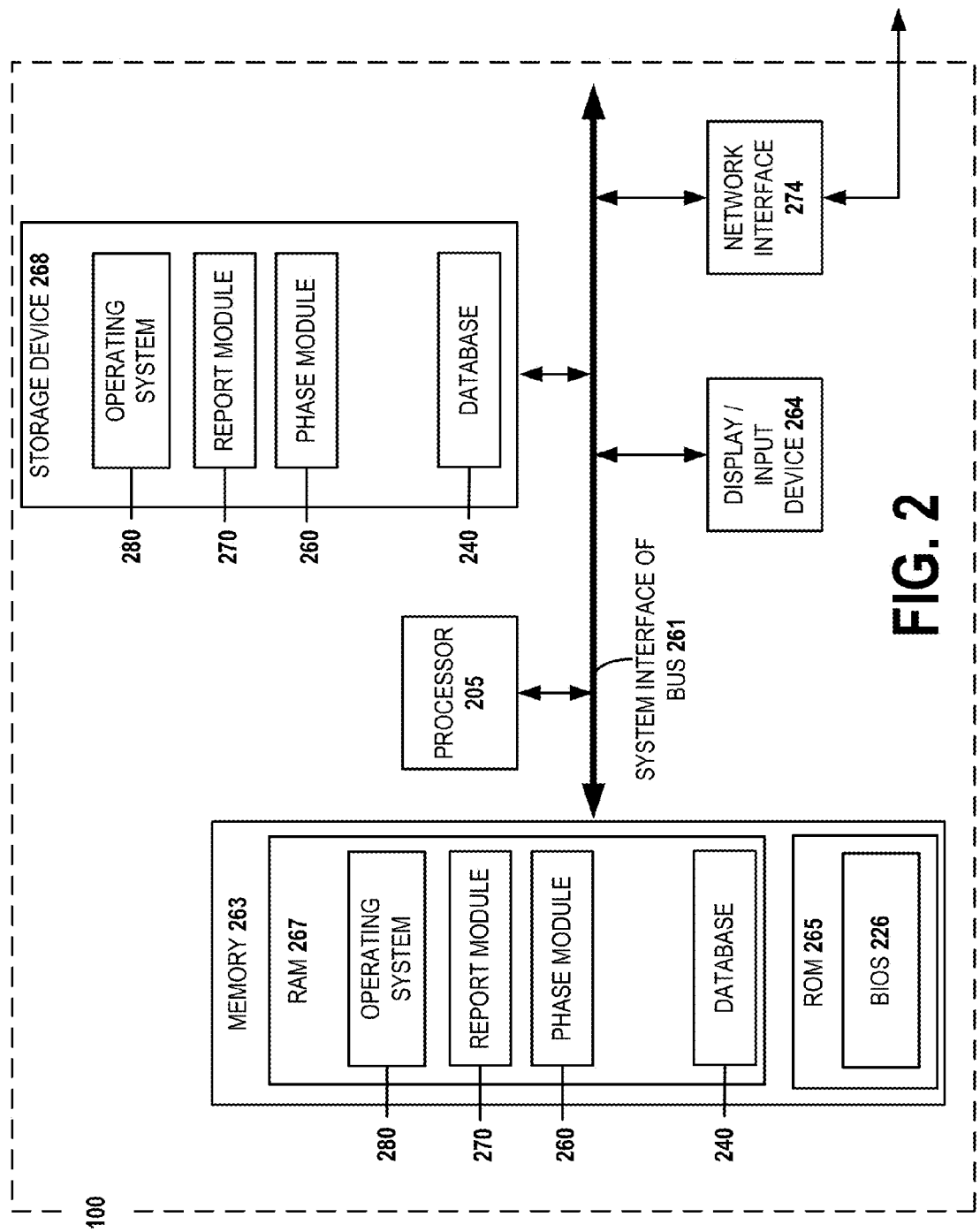
FIG. 2 is an exemplary schematic diagram of a management computing entity according to one embodiment of the present invention.

FIG. 2 provides a schematic of a management computing entity 100 according to one embodiment of the present invention. The management computing entity 100 can be used in a variety of settings, including a medical provider's facility. For example, the management computing entity 100 may manage information/data flows and processes for various computing entities by including, being associated with, or being in communication with a variety of computing entities, such as medication dispensing computing entities, vital sign monitors (including vaporizers, ventilators, pumps), medical record computing entities, data storage/facilitation computing entities, billing computing entities, medication computing entities, equipment computing entities, scheduling computing entities, and/or the like. In general, the term "computing entity" may refer to, for example, any computer, computing device, mobile phone, desktop, tablet, notebook or laptop, database management system, distributed system, server, blade, gateway, switch, processing device, or combination of processing devices adapted to perform the functions described herein.

As will be understood from FIG. 2, in one embodiment, the management computing entity 100 may include a processor 205 that communicates with other elements within the management computing entity 100 via a system interface or bus 261. The processor 205 may be embodied in a number of different ways. For example, the processor 205 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an exemplary embodiment, the processor 205 may be configured to execute instructions stored in memory or otherwise accessible to the processor 205. As such, whether configured by hardware or software methods, or by a combination thereof, the processor 205 may represent an entity capable of performing operations according to embodiments of the present invention when configured accordingly. For example, as discussed in more detail below, the management computing entity 100 may be configured, among other things, to receive, process, update, and/or store phase information/data associated with patients, medical procedures, medical providers, resource units, cases, and/or facilities. A display/input device 264 for receiving and displaying data may also be included in (or in communication with) the management computing entity 100. This display device/input device 264 may be, for example, a keyboard or pointing device that is used in combination with a monitor (e.g., an electronic screen/display). The display/input device 264 may be a touchscreen that can detect the presence and location of a touch within the display area. The management computing entity 100 may further include transitory and non-transitory memory 263, which may include both random access memory (RAM) 267 and read only memory (ROM) 265. The management computing entity's ROM 265 may be used to store a basic input/output system (BIOS) 226 containing the basic routines that help to transfer information to the different elements within the management computing entity 100.

In addition, in one embodiment, the management computing entity 100 may include at least one storage device 268, such as a hard disk drive, a CD drive, and/or an optical disk drive for storing information on various computer-readable media. The storage device(s) 268 and its associated computer-readable media may provide nonvolatile storage.

The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. Additionally, each of these storage devices 268 may be connected to the system bus 261 by an appropriate interface.

Furthermore, a number of executable instructions, applications, scripts, program modules, and/or the like may be stored by the various storage devices 268 and/or within RAM 267. Such executable instructions, applications, scripts, program modules, and/or the like may include an operating system 280 a report module 270, and a phase module 260. As discussed in more detail below, these executable instructions, applications, program modules, and/or the like may control certain aspects of the operation of the management computing entity 100 with the assistance of the processor 205 and operating system 280—although their functionality need not be modularized. In addition to the program modules, the management computing entity 100 may store or be in communication with one or more databases, such as database 240 comprising a record queue table. The record queue table may hold records that are used to process, update, and/or store information/data.

Also located within the management computing entity 100, in one embodiment, is a network interface 274 for interfacing with various computing entities, including a print computing entity. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the management computing entity 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the management computing entity's 100 components may be located remotely from other management computing entity 100 components. Furthermore, one or more of the components may be combined and additional components performing functions described herein may be included in the management computing entity 100.

2. Exemplary Data Interface Computing Entity

In one embodiment, the data interface computing entity 110 (e.g., with a data interface) may be used to monitor information/data, records, and/or record queues. The data interface computing entity 110 (e.g., via the data interface) can also request reports associated with the information/data, records, and/or record queues, create/generate/construct and send/transmit messages about the information/data, records, and/or record queues to various entities. To do so, the data interface may comprise executable instructions, applications, scripts, program modules, and/or the like to provide such functionality. Accordingly, the data interface computing entity 110 (e.g., via the data interface) may include components similar to those described with regard to the management computing entity 100. For example, the data interface computing entity 110 (e.g., with a data interface) may comprise: (1) a processor that communicates with other elements via a system interface or bus; (2) a display device/input device; (3) memory including both ROM and RAM; (4) a storage device; and (5) a network interface. As will be recognized, these architectures are provided for exemplary purposes only and are not limited to the various embodiments.

In one embodiment, the data interface computing entity 110 (e.g., via the data interface) can perform various operations and processes to create/generate/construct and send/transmit messages in a variety of formats. For example, in one embodiment, the data interface computing entity 110 (e.g., via the data interface) can create/generate/construct and send/transmit messages in compliance Health Level Seven International (HL7) and HBOCHI standards and formats. Such formats may include HL7 v2.3, HBOCHI v2.2b, HBOCHI 2.3b, and/or the like.

3. Exemplary Client/User Computing Entities

In one embodiment, client/user computing entities 115 may be used to receive messages (in a variety of formats including HL7 and HBOCHI) from the data interface computing entity 110. To do so, the client/user computing entities 115 may include components similar to those described with regard to the management computing entity 100 and/or the data interface computing entity 110. For example, the client/user computing entities 115 (e.g., with a data interface) may comprise: (1) a processor that communicates with other elements via a system interface or bus; (2) a display device/input device; (3) memory including both ROM and RAM; (4) a storage device; and (5) a network interface. As will be recognized, these architectures are provided for exemplary purposes only and are not limited to the various embodiments.

IV. EXEMPLARY SYSTEM OPERATION

Figure 3:
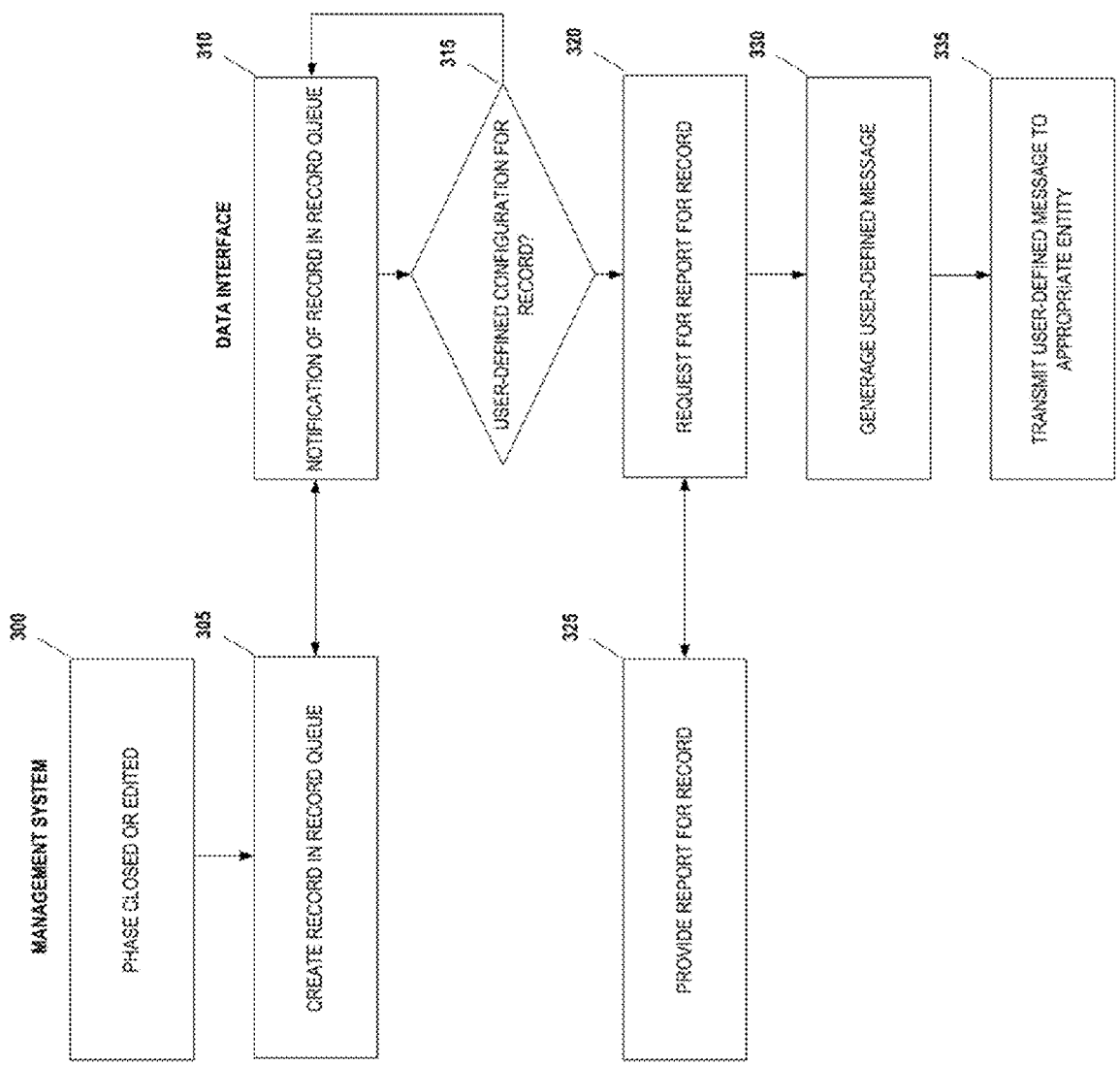
FIG. 3 is a flowchart illustrating operations and processes that can be used in accordance with various embodiments of the present invention.

Reference will now be made to FIGS. 3-14. FIG. 3 is a flowchart illustrating operations and processes that may be performed to provide user-defined messages. FIGS. 4, 5A, 5B, 6, 7A, and 7B show exemplary message formats. FIGS. 8-12 show the correlation between the exemplary message formats. FIG. 13 shows an exemplary report that can be used to create/generate/construct a user-defined message, such as the user-defined message shown in FIG. 14.

Although the following is described in the context of a medical environment, various embodiments of the present invention can be extended to other environments and be adapted to satisfy different needs and circumstances.

1. User-Defined Messaging Configurations

In one embodiment, a management computing entity 100 can receive, process, update, and/or store a variety of information/data. For example, the management computing entity 100 can receive, process, update, and/or store information/data associated with certain patients, medical procedures, medical providers, resource units, cases, and/or facilities. For instance, a surgical procedure may be associated with a preoperative phase, an intraoperative phase, and a postoperative phase. Thus, before, during, and/or after the preoperative phase, the management computing entity 100 may receive, process, update, and/or store phase information/data for the preoperative phase corresponding to a patient, a medical provider, a medical procedure, a resource unit, a case, and/or a facility. Similarly, the management computing entity 100 may receive, process, update, and/or store phase information/data for the intraoperative phase and/or the postoperative phase corresponding to a patient, a medical provider, a medical procedure, a resource unit, a case, and/or a facility.

In one embodiment, each time a given phase is closed and/or edited, the management computing entity 100 (e.g., via the phase module 260) can receive, process, update, and/or store the corresponding phase information/data (Block 300 of FIG. 3). To do so, the management computing entity may write a new record to a queue table (e.g., a record queue table in database 240) to process, update, and/or store the edited or closed phase information/data for the phase (Block 305 of FIG. 3). The management computing entity 100 may receive, process, update, and/or store phase information/data in accordance with a particular format, such as HL7 or HBOCHI. FIG. 4 shows an exemplary table header that may be used by the management computing entity 100 in understanding and/or interpreting the HL7 segment tables that are being referenced. Such segments may include a message header segment, a patient identification segment, a patient visit information segment, an observation segment, and/or an observation/result segment.

In one embodiment, when a client/user desires to interface with and/or receive information/data from a particular computing entity, such as the management computing entity 100, a user-defined messaging configuration can be created for any number of clients/users and stored, for example, in a user-defined messaging configuration file. The user-defined messaging configuration can define/identify the information/data that is of interest to a client/user. For example, a client/user may desire to interface with the management computing entity 100 to receive phase information/data regarding certain patients, medical procedures, medical providers, resource units, cases, and/or facilities.

In one embodiment, the user-defined messaging configuration may also define/identify the type of information/data (e.g., the type of phase information/data) that is of interest to a client/user. For example, for the preoperative phase, the client/user may desire to receive phase information/data associated with the patient's height, weight, date of birth, gender, name, race, address, marital status, citizenship, blood pressure, cholesterol, heart rate, medical provider, referring medical provider, consulting medical provider, temperature, credit rating, and/or the like. For the intraoperative phase, the client/user may desire to receive phase information/data associated with the start time of a surgical procedure, the medical provider performing the medical procedure, vital signs, diagnostics, types of samples collected, number of samples collected, and/or the like. Similarly, for the postoperative phase, the client/user may desire to receive phase information/data associated with the end time of the medical procedure, observations from the medical procedure, observation times, medications provided during the medical procedure, and/or the like.

In one embodiment, the user-defined messaging configuration may define/identify the format (e.g., a client/user format) in which the client/user desires to receive the information/data from the data interface computing entity 110, such as the formats shown in FIGS. 5A, 5B, and 6. Thus, the client/user format of the user-defined messaging configuration may define/identify the placement of the information/data in the segments and fields of user-defined messages. For instance, the client/user format may define/identify the specific segments of a line-by-line message to include the segments shown in FIG. 7A. The client/user format may also define/identify the specific segments of a reports-as-order-segments message to include the segments shown in FIG. 7B.

In one embodiment, the user-defined messaging configuration may define/identify how the segments and fields of the client/user format correlate to the segments and fields of the format used by the management computing entity 100 (e.g., HL7 or HBOCHI) to receive, process, update, and/or store information/data for the specific phases. For instance, FIGS. 8-12 show exemplary correlations from the client/user format to the format used by the management computing entity 100 to receive, process, update, and/or store information/data for the specific phases. As will be recognized, though, a variety of different formats and correlations can be used to adapt to various needs and circumstances.

In one embodiment, as part of the user-defined messaging configuration, report formats for creating user-defined messages (e.g., HL7 Observation Result (ORU) messages) can be defined/identified. That is, a user-defined messaging configuration may be associated with one or more report formats based on, for example, the patients, procedures, medical providers, resource units, cases, and/or facilities of interest. Then, the report formats can be used by the management computing entity 100 (e.g., via the report module 270) to provide various reports (to the data interface computing entity 110) with the information/data that is of interest to a client/user as defined by the user-defined messaging configuration. Each report may be associated with a report type and/or a report identifier, for example. The reports can be used to customize the information/data received by the data interface computing entity 110 (e.g., via the data interface) to create/generate/construct and send/transmit user-defined messages to a client/user—described in greater detail below.

In one embodiment, the format of the reports may be the layout of HL7 segments and fields. For example, the formats may allow for reports to be created/generated/constructed in a way that simulates HL7 order-related segments and the fields/data they contain, based on client/user needs. The reports may also include non-HL7 text (e.g., <segmentseparator>) within the report that can be used by the data interface computing entity 110 (e.g., via the data interface) to identify and separate the different segments and fields of information/data that are of interest to a client/user. In various embodiments, such an approach allows for the repeated implementation of the solution even if the information/data within a given report changes from client/user to client/user. For example, there may be one report format for the preoperative phase for client/user A. Similarly, there may be another report format for the intraoperative phase for client/user A. Further, there may be multiple report formats for the postoperative phase for client/user B, depending on, for example, the associated patient, medical provider, and/or facility.

FIG. 13 shows an exemplary report that includes information/data that is of interest to a particular client/user as defined by the user-defined messaging configuration. This report includes segments and fields with information/data available for the patient, procedure, medical provider, resource unit, case, and/or facility. In other words, the report can be used to collect the desired information/data and create/generate/construct, for example, the order-related segments and place the information/data in the segments, fields, and/or the like without having to create a custom interface. In one embodiment, the reports may contain information/data to be used as any segments that follow are determined by report contents (shown in FIG. 7B) in place of the OBR and/or OBX segments (shown in FIG. 7A) of the user-defined message. Such reports can be provided to the data interface computing entity 110 in a variety of formats, including text files, Word files, WordPerfect files, Hypertext Markup Language (HTML) files, OpenOffice files, portable document format (PDF) files, and/or the like.

Operatively, to create/generate/construct and send/transmit user-defined messages to clients/users that include information/data that is of interest, the data interface computing entity 110 (e.g., via the data interface) can request one or more reports from the management computing entity 100 in response to (e.g., after) certain triggers. In response to such requests, the management computing entity 100 can provide the requested reports to the data interface computing entity 110 (e.g., via the data interface). The reports can be provided in a text-based format or be converted by the data interface computing entity 110 (e.g., via the data interface) to a text-based format. Then, the data interface computing entity 110 (e.g., via the data interface) can use the information/data in the reports to create/generate/construct and send/transmit user-defined messages to clients/users (e.g., client/user computing entities 115) at the time desired and include the information/data desired.

In one embodiment, the user-defined messaging configuration may also define/identify the client/user computing entities 115 to which the user-defined messages should be sent/transmitted. For example, the user-defined messaging configuration may define/identify one or more email addresses, Internet Protocol (IP) addresses, device identifiers (e.g., Subscriber Identity Module (SIM) number, Media Access Control (MAC) address, International Mobile Subscriber Identity (IMSI) number, an Internet Protocol (IP) address, mobile equipment identifier (MEID)), and/or the like to which user-defined messages should be sent/transmitted.

As will be recognized, any number of user-defined messaging configurations can be created and stored, for example, as user-defined messaging configuration files. Further, as will be recognized, a variety of approaches and techniques can be used to adapt to various needs and circumstances.

2. Monitoring of Records

As indicated, each time a given phase is closed and/or edited, the management computing entity 100 (e.g., via the phase module 260) may write a new record to a record queue (e.g., a record queue table in database 240) to process, update, and/or store information/data about the edited or closed phase (Blocks 300, 305 of FIG. 3). The record may contain information/data that identifies the patient, procedure, medical provider, resource unit, case, and/or facility corresponding to the edited or closed phase. Thus, in one embodiment, after one or more user-defined messaging configurations and one or more reports have been defined/identified, the data interface computing entity 110 (e.g., via the data interface) can monitor a record queue (e.g., a record queue table in database 240) for new records. To receive notification that a new record is in the record queue (e.g., a record queue table in database 240), the data interface computing entity 110 (e.g., via the data interface) can regularly, periodically, and/or continuously poll the management computing entity 100.

By way of example, assuming a patient (e.g., John Doe) has just completed the preoperative phase of his medical procedure and has been moved to an operating room, an appropriate medical provider can close John Doe's preoperative phase (e.g., by inputting phase information/data into a computing entity). In response to (e.g., after) receiving the phase information/data indicating the preoperative phase for John Doe has been closed, the management computing entity 100 can write a record to the record queue (e.g., a record queue table in database 240) to process, update, and/or store the closed phase information/data. As a result of the regular, periodic, and/or continuous polling of the management computing entity 100, the data interface computing entity 110 (e.g., via the data interface) can receive a notification that the new record for John Doe has been written to the record queue (e.g., a record queue table in database 240), as indicated in Block 310 of FIG. 3.

3. User-Defined Messaging Configuration for Records and User-Defined Messages

In one embodiment, as indicated, the data interface computing entity 110 (e.g., via the data interface) can receive a notification when a new record is written to the record queue (e.g., a record queue table in database 240). In response to (e.g., after) a notification that a new record has been written to the record queue (e.g., a record queue table in database 240), the data interface computing entity 110 (e.g., via the data interface) can determine whether the record is associated with a user-defined messaging configuration (Block 315 of FIG. 3) by, for example, cross referencing the user-defined messaging configuration files. By doing so, the data interface computing entity 110 (e.g., via the data interface) can determine whether the record is associated with a patient, medical procedure, medical provider, resource unit, case, and/or facility, for example, that corresponds to one or more user-defined messaging configurations.

In one embodiment, if the record is associated with a user-defined messaging configuration, the data interface computing entity 110 (e.g., via the data interface) can request patient, medical procedure, medical provider, resource unit, case, and/or facility information/data that is necessary for creating/generating/constructing a user-defined message as defined/identified by the user-defined messaging configuration. The request may be sent to any appropriate computing entity, including the management computing entity 100. After receiving the necessary patient, medical procedure, medical provider, resource unit, case, and/or facility information/data, the data interface computing entity 110 (e.g., via the data interface) can begin creating/generating/constructing at least part of a user-defined message (Block 330 of FIG. 3). For example, the data interface computing entity 110 (e.g., via the data interface) can create/generate/construct a "shell" for a user-defined message (e.g., HL7 ORU message) to include the appropriate patient, medical procedure, medical provider, resource unit, case, and/or facility information/data. The shell of the user-defined message (e.g., HL7 ORU message) may include, for example, the MSH, PID, and PV1 segment parts of the message (see FIGS. 7A and 7B).

Additionally or alternatively, if there is a user-defined messaging configuration associated with the record, the data interface computing entity 110 (e.g., via the data interface) can request the report defined/identified by the user-defined messaging configuration corresponding to the record (Block 320 of FIG. 3). The request for the report can be sent to a variety of appropriate computing entities, including the management computing entity 100 and/or a print computing entity. The request for the report may include information/data that can be used to identify the patient, medical procedure, medical provider, resource unit, case, and/or facility to which the report corresponds. The request for the report may also include a report type and/or report identifier for the specific report that should be provided for the patient, medical procedure, medical provider, resource unit, case, and/or facility.

In response to (e.g., after) the appropriate computing entity (the management computing entity 100 and/or a print computing entity) receiving the request for the report, the appropriate computing entity (the management computing entity 100 and/or a print computing entity) can create/generate/construct and send/transmit the appropriate report to the data interface computing entity 110 (e.g., via the data interface), as indicated in Block 325 of FIG. 3. The data interface computing entity 110 (e.g., via the data interface) can then receive the report. If the report is in a text-based format, the data interface computing entity 110 (e.g., via the data interface) can select the appropriate information/data from the report to include in the user-defined message. If the report is not in a text-based format, the data interface computing entity 110 (e.g., via the data interface) can convert the report to a text-based format and then select the appropriate information/data from the report to include in the user-defined message.

In one embodiment, with the information/data selected from the report, the data interface computing entity 110 (e.g., via the data interface) can complete creation/generation/construction of the user-defined message (e.g., HL7 ORU message) by combining the selected information/data from the report with the previously created/generated/constructed shell. In one embodiment, based on the user-defined message configuration, the data interface computing entity 110 (e.g., via the data interface) may replace the pre-defined <segmentseparator> instances in the selected text, for example, into HL7 carriage returns that separate the order segments within the report. In various embodiments, this approach may allow what would otherwise be basic text to be broken up into orderly HL7 segments of information/data. The data interface computing entity 110 (e.g., via the data interface) can then append the text selected from the report to the shell of the user-defined message (e.g., HL7 ORU message) that was previously created (Block 330 of FIG. 3). Thus, completing the creation/generation/construction of the user-defined message (e.g., HL7 ORU message) may include creating/generating/constructing the PV1, OBR, and/or OBR segments (shown in FIGS. 7A and 7B) of the user-defined message from the information/data in the report.

As described, the data interface computing entity 110 (e.g., via the data interface) can first create/generate/construct part of the user-defined message (e.g., HL7 ORU message) and use a flexible report to create/generate/construct the remainder of the user-defined message (e.g., HL7 ORU message). In various embodiments, such an approach provides an interface that remains supportable and easy to implement and maintain even while providing custom-like output that can meet a client's/user's needs. As will be recognized, a variety of other approaches and techniques can be used to adapt to various needs and circumstances.

In one embodiment, the data interface computing entity 110 (e.g., via the data interface) can then persist the completed user-defined message to, for example, a buffer file of the interface before it is sent/transmitted to the appropriate client/user computing entities 115. The data interface computing entity 110 (e.g., via the data interface) can then pick up the created/generated/user-defined message (e.g., HL7 ORU message) and send/transmit the message to the appropriate client/user computing entities 115 (e.g., using a variety of protocols such as Transmission Control Protocol (TCP)/IP), as indicated Block 335 of FIG. 3. Any number of user-defined messages can be created/generated/constructed and transmitted on a periodic, regular, and/or continuous basis.

V. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for providing a user-defined message, the method comprising:
   receiving, via one or more processors, a notification that a new record is in a record queue in response to detecting an indication that an operative phase, among a plurality of identified phases, of a surgical medical procedure being performed on a patient is being closed or edited;
   responsive to receiving the notification that the new record is in the record queue, determining, via the one or more processors, that the new record is associated with a user-defined messaging configuration defining different data items of interest, according to a designated health standard protocol, corresponding to each of the plurality of identified phases of the surgical medical procedure, the defined different data items of interest of each of the plurality of identified phases are designated for respective different communication devices;
   after determining that the new record is associated with a user-defined messaging configuration, requesting, via the one or more processors, a report associated with the new record corresponding to the user-defined messaging configuration, the request identifying (a) a patient to which the report corresponds and (b) a report type;
   receiving, via the one or more processors, the report associated with the new record, the report generated, in part, according to predefined segments and predefined fields of the designated health standard protocol with information that is specified of interest in the user-defined messaging configuration; and
   generating, via the one or more processors, a user-defined message based at least in part on the new record and the report associated with the new record.

2. The method claim 1 further comprising converting the report to a text-based format.

3. The method claim 2, wherein the user-defined message for the new record comprises text selected from the report.

4. The method claim 1, wherein the record queue comprises a record queue table.

5. The method claim 1, wherein the notification that the new record is in the record queue is received in response to polling.

6. The method claim 1 further comprising transmitting the user-defined message to one or more computing entities.

7. The method of claim 1, wherein prior to receiving the report, the method further comprises:

specifying in the user-defined messaging configuration a format in which one or more communication devices desire to receive information regarding the phases of the surgical medical procedure.

8. An apparatus comprising at least one processor and at least one memory including computer program code, the at least one memory and the computer program code configured to, with the processor, cause the apparatus to at least:
receive a notification that a new record is in a record queue in response to detecting an indication that an operative phase, among a plurality of identified phases, of a surgical medical procedure being performed on a patient is being closed or edited;
responsive to receiving the notification that the new record is in the record queue, determine that the new record is associated with a user-defined messaging configuration defining different data items of interest, according to a designated health standard protocol, corresponding to each of the plurality of identified phases of the surgical medical procedure, the defined different data items of interest of each of the plurality of identified phases are designated for respective different communication devices;
after determining that the new record is associated with a user-defined messaging configuration, request a report associated with the new record corresponding to the user-defined messaging configuration, the request identifying (a) a patient to which the report corresponds and (b) a report type;
receive the report associated with the new record, the report generated, in part, according to predefined segments and predefined fields of the designated health standard protocol with information that is specified of interest in the user-defined messaging configuration; and
generate a user-defined message based at least in part on the new record and the report associated with the new record.

9. The apparatus claim 8, wherein the memory and computer program code are further configured to, with the processor, cause the apparatus to convert the report to a text-based format.

10. The apparatus claim 9, wherein the user-defined message for the new record comprises text selected from the report.

11. The apparatus claim 8, wherein the record queue comprises a record queue table.

12. The apparatus claim 8, wherein the notification that the new record is in the record queue is received in response to polling.

13. The apparatus claim 8, wherein the memory and computer program code are further configured to, with the processor, cause the apparatus to transmit the user-defined message to one or more computing entities.

14. The apparatus of claim 8, wherein prior to receive the report, the memory and computer program code are further configured to, with the processor, cause the apparatus to:
specify in the user-defined messaging configuration a format in which one or more communication devices desire to receive information regarding the phases of the surgical medical procedure.

15. A computer program product for providing a user-defined message, the computer program product comprising at least one non-transitory computer-readable storage medium having computer-readable program code portions stored therein, the computer-readable program code portions comprising:
an executable portion configured to receive a notification that a new record is in a record queue in response to detecting an indication that an operative phase, among a plurality of identified phases, of a surgical medical procedure being performed on a patient is being closed or edited;
an executable portion configured to, responsive to receiving the notification that the new record is in the record queue, determine that the new record is associated with a user-defined messaging configuration defining different data items of interest, according to a designated health standard protocol, corresponding to each of the plurality of identified phases of the surgical medical procedure, the defined different data items of interest of each of the plurality of identified phases are designated for respective different communication devices;
an executable portion configured to after determining that the new record is associated with a user-defined messaging configuration, request a report associated with the new record corresponding to the user-defined messaging configuration, the request identifying (a) a patient to which the report corresponds and (b) a report type;
an executable portion configured to receive the report associated with the new record, the report generated, in part, according to predefined segments and predefined fields of the designated health standard protocol with information that is specified of interest in the user-defined messaging configuration; and
an executable portion configured to generate a user-defined message based at least in part on the new record and the report associated with the new record.

16. The computer program product claim 15 further comprising an executable portion configured to convert the report to a text-based format.

17. The computer program product claim 16, wherein the user-defined message for the new record comprises text selected from the report.

18. The computer program product claim 15, wherein the record queue comprises a record queue table.

19. The computer program product claim 15, wherein the notification that the new record is in the record queue is received in response to polling.

20. The computer program product claim 15 further comprising an executable portion configured to transmit the user-defined message to one or more computing entities.

21. The computer program product of claim 15, wherein prior to receive the report, the computer program product further comprising:
an executable portion configured to specify in the user-defined messaging configuration a format in which one or more communication devices desire to receive information regarding the phases of the surgical medical procedure.

* * * * *